United States Patent [19]

Mikkelsen

[11] Plant 5,161

[45] Dec. 20, 1983

[54] BEGONIA PLANT NAMED LYRIC

[75] Inventor: James C. Mikkelsen, Ashtabula, Ohio

[73] Assignee: Mikkelsens, Inc., Ashtabula, Ohio

[21] Appl. No.: 418,490

[22] Filed: Sep. 15, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A begonia named Lyric having white double flowers, dark green, firm to crisp glabrous foliage with serrated edges, excellent keeping qualities, and continuous year round flowering.

1 Drawing Figure

1

The present invention relates to a new and distinctive cultivar of begonia plant, botanically known as Hiemalis begonia (Fotsch), and referred to by the cultivar name Lyric. Lyric is a spontaneous mutation of the begonia cultivar Encore and was observed in a group of flowering 10 cm. potted plants of Encore. Encore is disclosed in my pending application Ser. No. 418,489, filed Sept. 15, 1982. Asexual reproduction by leaf cuttings has reproduced the unique features of the new cultivar through successive propagations.

The following characteristics distinguish the new begonia from both its parents and other begonias commercially known and used in the floriculture industry:

1. Except for the white flowers, the general characteristics of Encore are applicable for Lyric.

2. The foliage of both Encore and Lyric is unique, with sharp serrations that are retained through maturity of the leaf. Foliage is crisp yet not brittle.

3. Lyric is above average in number of flowers produced per stem. The keeping quality of flowers is excellent, and the flower color is a clear pleasing white.

4. Propagation by leaf cuttings is extremely good, consistently producing 5–6 or more adventitious shoots per petiole. Total propagation time is slower by 7–10 days than many present commercial cultivars.

5. Plant growth is also somewhat slower so that Lyric is more ideally suited for 10–12 cm. pots than larger containers. Highly sensitive to normal rates of growth regulators Cycocel and A-Rest.

6. Lyric has exceptional keeping qualities for both foliage and flowers, making it ideal for mass distribution.

The accompanying colored photograph taken July, 1982 illustrates in perspective view the overall appearance of Lyric grown in a 10 cm plastic pot, and showing the colors as true as it is reasonably possible to obtain in a colored reproduction of this type.

The following is a detailed description of my new begonia cultivar based on plants produced under commercial practices at the greenhouses of Mikkelsens Inc., Ashtabula, Ohio 44004. Color references are mae to The Royal Horticultural Society Colour Chart except where general color terms of ordinary dictionary significance are used.

Parentage: A white flower mutation of hiemalis begonia cultivar Encore.

Propagation:

(A) *Type cutting.*—Leaf cuttings.

2

(B) *Time to root.*—25–28 days at 21° C. summer, 30 to 35 days at 21° C. winter.

(C) *Rooting habit.*—Abundant, fibrous, dendritic.

(D) *Time for shoot development.*—Shoot initiation and development is slow, taking up to 12 weeks in summer to 15 weeks in winter. Shoot count is high per leaf cutting.

Plant Description:

(A) *Form.*—Low, compact, bush type plant; herbaceous.

(B) *Habit of growth.*—Sturdy, upright slow growth with considerable self-branching, combined with good adventitious shoot count make a well rounded uniform looking plant.

(C) *Foliage.*—Simple, alternate, borne on strong semi-rigid petioles. (1) Size: Generally small, up to 6–8 cm. from base to apex. (2) Shape: Orbicular cleft serrated having an appearance of maple leaf. (3) Texture: Firm, crisp but not brittle, glabrous on top, rugose underside. (4) Margin: Serrated. (5) Color: Young foliage top side, green 137A; underside, red 181A with green veins protruding; mature foilage top side green 137A with slight red overtone; under side, yellow green 148B with red pigmentation. (6) Venation: Palmate.

Flowering description:

(A) *Flowering habit.*—Flowering is presented in a raceme, with flowering continuing with secondary buds developing below the primary flowers.

(B) *Natural flowering season.*—Generally flowers year round after developing some maturity. Once flowering has initiated, plants will continue to flower up to twelve months.

(C) *Flower bud description.*—Flat, nearly round, tending to heart-shape.

(D) *Flowers borne.*—On small but sturdy pedicels originating from strong peduncles result in the raceme form of terminal flower blooming first and additional flowering progressing as raceme develops.

(E) *Quantity.*—Flowering is abundant with 12–15 flowers open at one time per peduncle.

(F) *Tepals.*—(1) Shape: Slightly oval. (2) Color top side in winter when opening, white 155A, underside of basal tepals, yellow green 145C, sometimes with pinking. (3) Number of tepals: Generally 12. (4) Size of tepals: 2 cm. (5) Flower size: 3.5 to 4 cm.

(G) *Reproductive organs.*—A sterile triploid.

Disease resistance: To date the new cultivar appears to be highly resistant to powdery mildew when produced in areas of other begonias infected with this problem.

I claim:

1. A new and distinct cultivar of begonia named

Lyric, as described and illustrated, and particularly characterized by its double white flowers with ruffled edges; dark green, firm to crisp glabrous foliage with serrated edges; excellent keeping qualities, and continuous year round flowering.

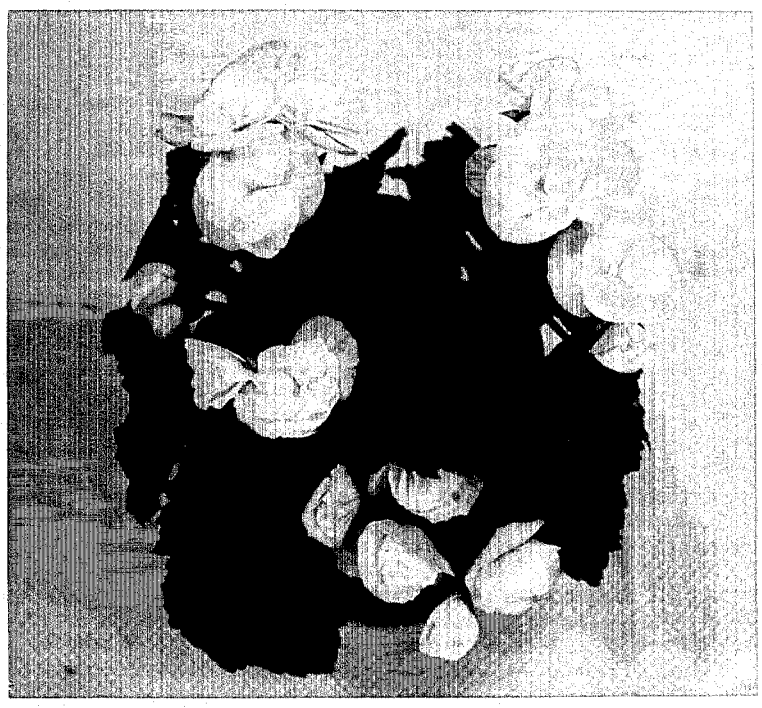

* * * * *